(12) United States Patent
Li

(10) Patent No.: US 7,570,353 B2
(45) Date of Patent: Aug. 4, 2009

(54) FABRICATION AND TEST METHODS AND SYSTEMS

(75) Inventor: Hong-Jyh Li, Austin, TX (US)

(73) Assignee: Infineon Technologies AG, Munich (DE)

( * ) Notice: Subject to any disclaimer, the term of this patent is extended or adjusted under 35 U.S.C. 154(b) by 593 days.

(21) Appl. No.: 11/305,801

(22) Filed: Dec. 16, 2005

(65) Prior Publication Data

US 2007/0138465 A1    Jun. 21, 2007

(51) Int. Cl.
*G01N 21/00* (2006.01)
(52) U.S. Cl. .................. 356/237.2; 356/237.5
(58) Field of Classification Search ... 356/237.1–237.5, 356/364–369; 438/16
See application file for complete search history.

(56) References Cited

U.S. PATENT DOCUMENTS

| | | | | |
|---|---|---|---|---|
| 4,211,488 | A | * | 7/1980 | Kleinknecht ................ 356/369 |
| 5,042,952 | A | * | 8/1991 | Opsal et al. .................. 356/432 |
| 6,147,507 | A | * | 11/2000 | Shabde et al. ............... 324/766 |
| 6,884,640 | B2 | | 4/2005 | Peterson et al. |
| 7,446,474 | B2 | * | 11/2008 | Maldonado et al. ......... 313/542 |
| 7,465,591 | B2 | * | 12/2008 | Borden et al. ................. 438/16 |

OTHER PUBLICATIONS

Hayzelden, C., "Gate Dielectric Metrology," Handbook of Silicon Semiconductor Metrology, 2001, pp. 17-47, Chapter 2, Marcel Dekker, Inc., New York, NY.
"Spectroscopic Ellipsometers and Thin Film Characterization," http://www.jawoollam.com, downloaded Dec. 9, 2005, 2pp., J.A. Woollam Co., Inc., Lincoln, NE.
Takeuchi, H., et al., "Observation of Bulk HfO$_2$ Defects by Spectroscopic Ellipsometry," J. Vac. Sci. Technol. A, Jul./Aug. 2004, pp. 1337-1341, vol. 22, No. 4, American Vacuum Society, Research Triangle Park, NC.
"WVASE 32® Elipsometry Analysis Software," http://www.jawoollam.com, downloaded Dec. 9, 2005, 2 pp., J. A. Woollam co., Inc., Lincoln, NE.

* cited by examiner

*Primary Examiner*—Hoa Q Pham
(74) *Attorney, Agent, or Firm*—Slater & Matsil, L.L.P.

(57) ABSTRACT

Methods and systems for fabricating and testing semiconductor devices are disclosed. In one embodiment, a method of forming a material includes providing a first workpiece, forming a material on the first workpiece using a first process condition, and measuring a defect state of the material using a test that utilizes a monochromatic light source. If the defect state is below a predetermined value, the material is formed on at least one second workpiece using the first process condition.

10 Claims, 8 Drawing Sheets

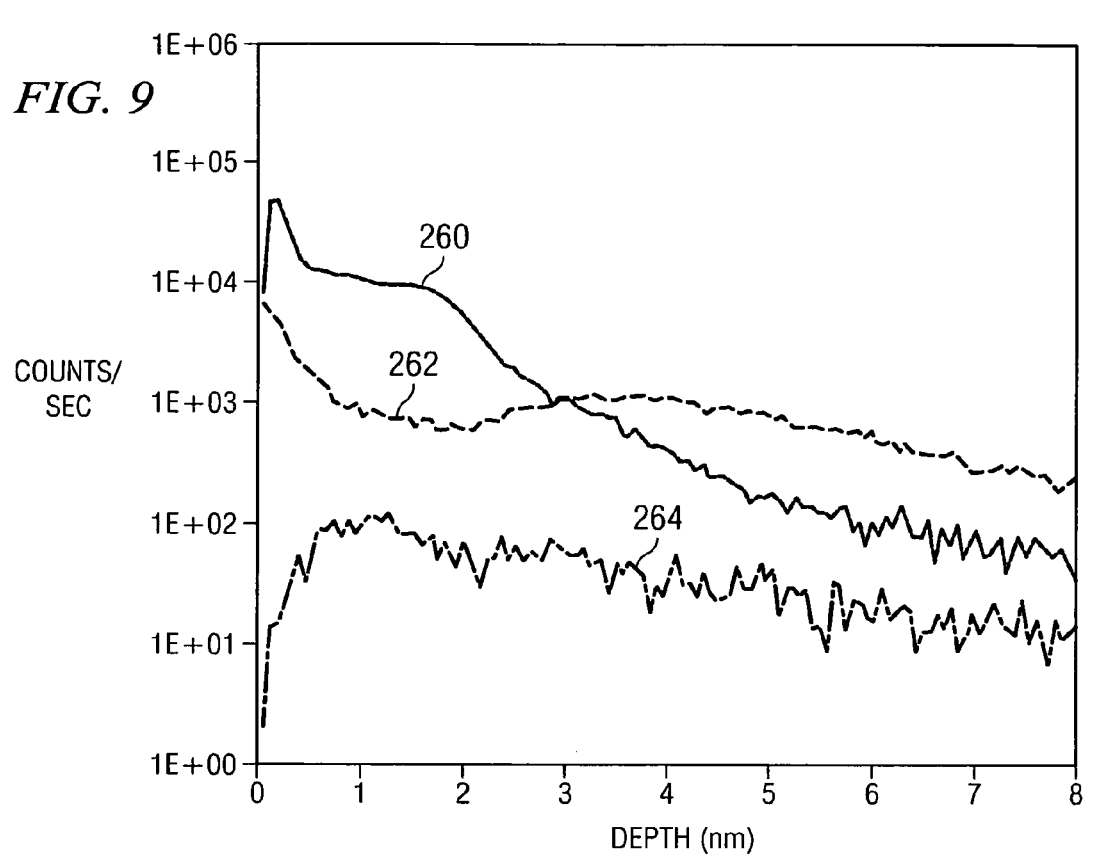
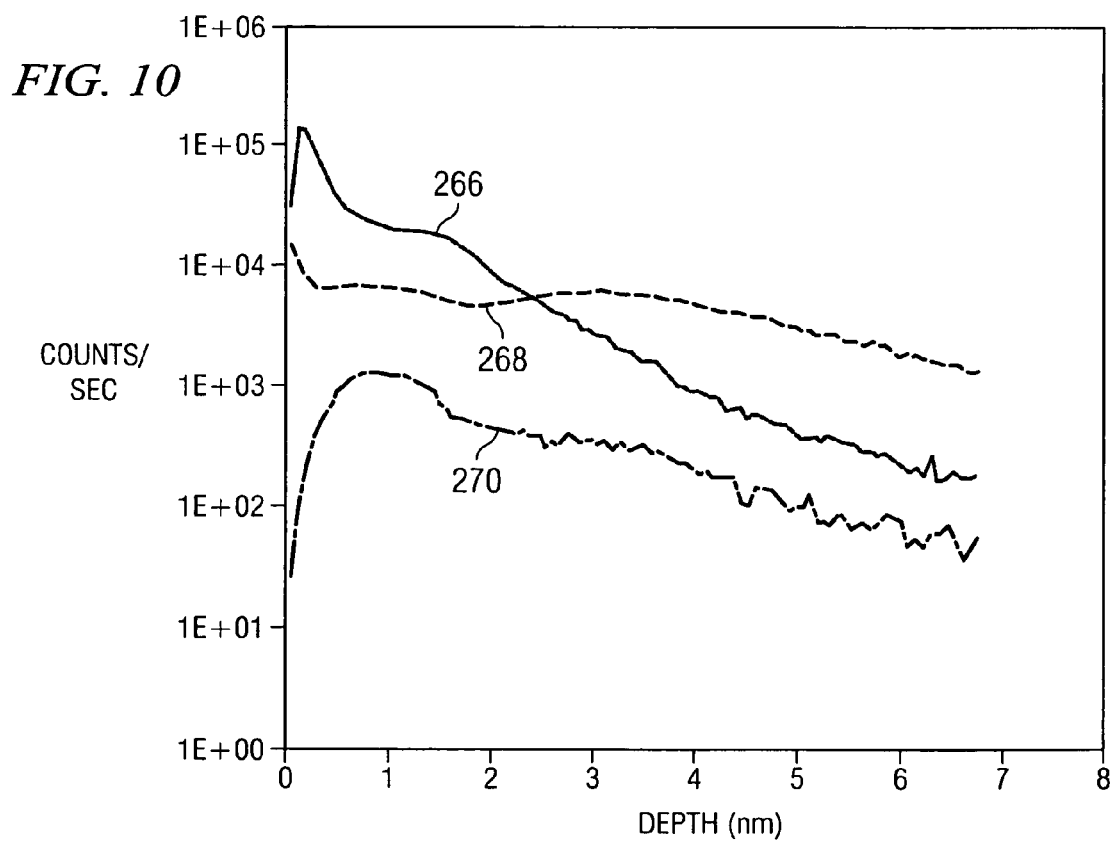

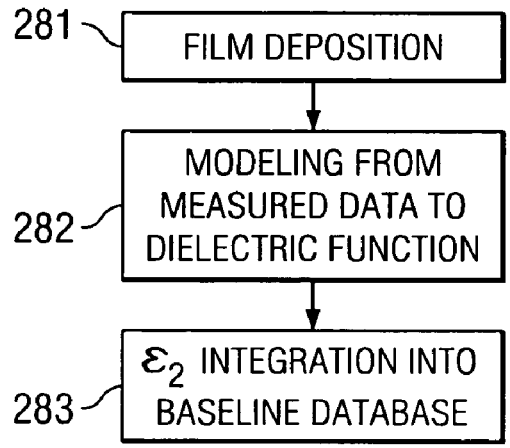
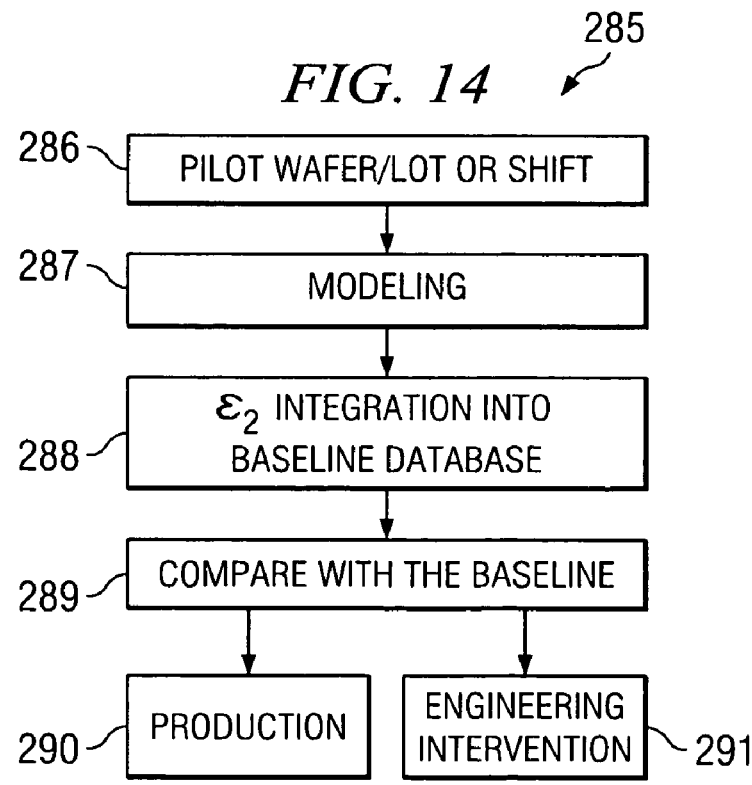

US 7,570,353 B2

FABRICATION AND TEST METHODS AND SYSTEMS

TECHNICAL FIELD

The present invention relates generally to the fabrication and testing of semiconductor devices, and more particularly to the evaluation of the quality of material layers formed on semiconductor devices.

BACKGROUND

Semiconductor devices are used widely in many applications, such as computers, televisions, home appliances, automobiles, cellular phones, and many other electrical and mechanical devices. Semiconductor devices are manufactured by depositing many thin layers of insulating, conductive, and semiconductor materials over a semiconductor substrate, and patterning the various layers using lithography.

There is a trend in the semiconductor industry towards downscaling or reducing the size of semiconductor features, in order to reduce the size and weight of the devices the semiconductor devices are used in, and to increased speed and decrease power consumption of devices, as examples. The thickness of material layers is also being decreased. Many material layers are extremely thin, for example, comprising only a few nanometers (nm) or Angstroms in thickness, for example.

The quality of a material layer of a semiconductor device is very important for device performance in order to achieve the device operation required. Unfortunately, the quality of some material layers may not be detectable until after the fabrication of a semiconductor device is completed, which results in entire lots of semiconductor devices needing to be scrapped, and further resulting in increased manufacturing time and costs. Furthermore, some tests to detect quality are destructive so that they may only be performed on samples of wafers, and the integrated circuits are destroyed in the test process.

Thus, what are needed in the art are improved methods and systems for evaluating the quality of material layers at various stages of a manufacturing cycle, e.g., part-way into a manufacturing cycle of a semiconductor device.

SUMMARY OF THE INVENTION

These and other problems are generally solved or circumvented, and technical advantages are generally achieved, by preferred embodiments of the present invention, which provide novel methods and systems for fabricating and testing semiconductor devices.

In accordance with a preferred embodiment of the present invention, a method of forming a material includes providing a first workpiece, forming a material on the first workpiece using a first process condition, and measuring a defect state of the material using a test that utilizes a monochromatic light source. If the defect state is below a predetermined value, the material is formed on at least one second workpiece using the first process condition.

The foregoing has outlined rather broadly the features and technical advantages of embodiments of the present invention in order that the detailed description of the invention that follows may be better understood. Additional features and advantages of embodiments of the invention will be described hereinafter, which form the subject of the claims of the invention. It should be appreciated by those skilled in the art that the conception and specific embodiments disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which:

FIGS. 9 and 10 show destructive test results for HfSiON films;

FIG. 13 is a flow chart for establishing a baseline for the test methods described herein;

FIG. 14 is a flow chart for implementing the test method in accordance with an embodiment of the present invention;

Corresponding numerals and symbols in the different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

Figure 1:
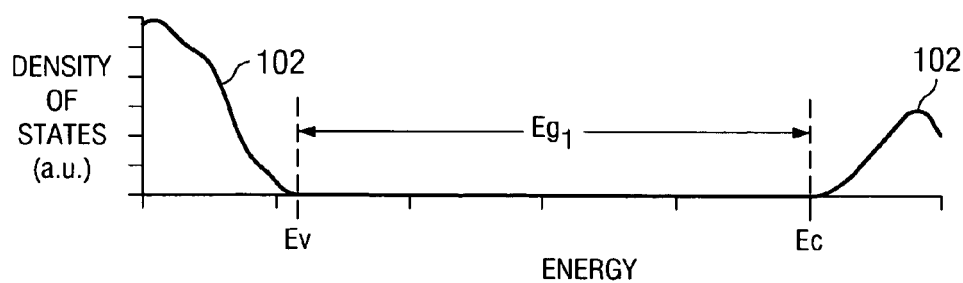
FIG. 1 shows an ideal graph of the density of state for an ideal dielectric or insulating material which has zero density of states for the energy within a band gap range.

The making and using of the presently preferred embodiments are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The present invention will be described with respect to preferred embodiments in a specific context, namely in the fabrication of semiconductor devices. The invention may also be applied, however, to other applications where thin films of material are formed, and where it is desirable to test the quality of the thin films of material, for example. The terms "film" and "material layer" are used interchangeably herein.

Embodiments of the present invention comprise novel testing methods and systems that are described herein for evaluating the quality of dielectric material layers formed on a semiconductor workpiece. However, embodiments of the present invention may also be used to evaluate the quality of semiconductive material layers, as examples.

Silicon dioxide ($SiO_2$), silicon nitride ($Si_xN_y$), and silicon oxynitride (SiON) are dielectric materials that have been used for many years as insulating material layers in semiconductor devices. These dielectric materials have a dielectric constant $k_1$ of about 3.9 ($SiO_2$), 7.8 ($Si_xN_y$), and between about 3.9 and 7.8 (SiON), as examples. In some semiconductor devices, such as transistors, there is a trend towards the use of high dielectric constant ($k_1$) dielectric materials, e.g., as a dielectric material for a gate dielectric of transistors. Because the letter "k" is used to represent two parameters in this discussion, the dielectric constant of a material will be referred to as "$k_1$," herein, for example.

High $k_1$ dielectric materials have a $k_1$ value that is greater than the dielectric constant of $SiO_2$, and may comprise a $k_1$ value of about 4.0 or greater, for example. Some high $k_1$ dielectric materials that are being evaluated for use as a dielectric material in semiconductor devices include $HfO_2$, $HfSiO_x$, $Al_2O_3$, $ZrO_2$, $ZrSiO_x$, $Ta_2O_5$, $La_2O_3$, $SiO_2$, $TiO_2$, $CeO_2$, $Bi_4Si_2O_{12}$, $WO_3$, $Y_2O_3$, $LaAlO_3$, BST ($Ba_{(a-x)}Sr_x$-$TiO_3$), PST ($PbSc_xTa_{(1-a)}O_3$), nitrides thereof, $Si_xN_y$, SiON, $HfAlO_x$, $HfAlO_xN_{1-x-y}$, $ZrAlO_x$, $ZrAlO_xN_y$, $SiAlO_x$, $SiAlO_xN_{1-x-y}$, $HfSiAlO_x$, $HfSiAlO_xN_y$, $ZrSiAlO_x$, $ZrSiAlO_xN_y$, PZN ($PbZn_xNb_{(1-x)}O_3$), PZT ($PbZr_xTi_{(1-x)}O_3$), PMN ($Pb$-$Mg_xNb_{(1-x)}O_3$), combinations thereof, or multiple layers thereof, or combinations or multiple layers thereof with SiO2, SixNy, and/or SiON, as examples.

In transistors, using a gate dielectric material having a high $k_1$ value allows the physical thickness of the gate dielectric to be increased, reducing leakage current with comparable device capacitance. As the equivalent oxide thickness (EOT) of the gate dielectric is scaled down to the sub-nm regime, the gate leakage ($J_g$) will need to be further reduced for many applications, for example.

However, some high $k_1$ dielectric materials have a poor film quality when deposited. Defects may be present in the atomic structure, for example. High $k_1$ dielectric materials such as $HfO_2$ and $HfSiO_x$ have been observed to suffer from oxygen vacancies, impurities (e.g., from precursors used to deposit the high $k_1$ dielectric materials), and defects (e.g., at grain boundaries). These defects manifest themselves in traps or defect states in the band diagram of the materials.

These high $k_1$ dielectric quality problems or film imperfections have been observed to be a source of mobility degradation, threshold voltage ($V_t$) instability, and various reliability issues, when these high $k_1$ dielectric materials are used as gate dielectrics of transistors, for example. For example, $HfO_2$ has been observed to have more defect states than some other high $k_1$ dielectric materials, which causes a larger hysteresis in the capacitance-voltage (CV) curve of the transistor and degraded channel mobility.

A problem with the fabrication and testing of high $k_1$ dielectric materials is that there is currently no in-line (e.g., that may be readily implemented in a manufacturing process flow or production line) detection technique to "see" or detect imperfections in the film quality, that can be improved by process controls or other means. Thus, the film quality of materials such as high $k_1$ dielectric materials cannot be discovered until devices are manufactured, for example.

Film imperfections can be introduced by the instability of the deposition tool used to deposit or form the material layer, for example. Film quality may be affected by the precursor levels and the air flows. These processing parameters need to be controlled on a frequent, e.g., daily, basis in a semiconductor manufacturing facility, e.g., by mapping between the various processing parameters and the film quality to obtain repeatable film quality results. Currently, the control of these processing parameters is attempted using the gauges and valves of the deposition tools. However, the gauges and valves of deposition tools often cannot distinguish between the fluctuations of the air flows in terms of chemical composition, for example, which is important in controlling parameters of the film quality control. Thus, the stability of a deposition tool is difficult to gauge and detect, for example.

Charge trapping and film imperfections of dielectric materials may be measured after devices are manufactured using bench tests to measure electrical characteristics of the devices after the formation of metallization layers of the devices, such as single pulse tests, constant voltage stress tests, and negative bias temperature instability (NBTI), as examples. However, this approach to film quality detection is costly, time consuming, and the results are often inconclusive. For example, from gate dielectric deposition to upper level metallization layer formation and subsequent testing, many processing steps are required; e.g., many lithography steps are required to pattern the various material layers. If fatal imperfections exist in terms of film quality after the dielectric film deposition, the subsequent processing steps to form the metallization layers are wasteful in terms of both money and time. Furthermore, because there are many processing steps after the gate dielectric deposition to the formation of the metallization layers, the test results after the metallization layer formation are difficult to directly link to the process parameters of the dielectric deposition and hence, the tests are inclusive for the dielectric film quality indication.

There are off-line (e.g., not implementable in a manufacturing production line) methods of detecting film quality using physical analysis, such as secondary ion mass spectrometry (SIMS), X-ray photoelectron spectroscopy (XPS), and Fourier transform infrared spectroscopy (FTIR), as examples. However, SIMS is a destructive test, and thus is difficult to execute on a daily basis and on a device wafer level. Furthermore, XPS and FTIR do not reveal defect state information.

Thus, improved methods of testing and evaluating the quality of films formed on semiconductor devices that are non-destructive and that may be implemented in-line in manufacturing process flows are needed in the art.

Embodiments of the present invention utilize spectroscopy ellipsometry (SE) to provide in-line test methods for determining the quality of dielectric films. The dielectric quality detection methods disclosed here include dielectric quality characterization methods, in-line production monitor protocols to control the quality of the dielectric method in the manufacturing process, and metrology tools suitable for manufacturing to execute the protocols, as examples. Some background technology for the novel test methods and systems of the present invention will next be described.

Spectroscopy ellipsometry is a technique that may be used to measure the defect state. Spectroscopy ellipsometry has been used to obtain thin film thicknesses of semiconductor devices, for example. This application of spectroscopy ellipsometry has been well established in the semiconductor industry, and thus, the details of SE used for film thickness measurement is not described herein. Hayzelden, C. describes hardware settings, physics, and procedures for metrology such as SE for gate dielectric measurement, in "Gate Dielectric Metrology," Handbook of Silicon Semiconductor Metrology, 2001, pp. 17-47, Chapter 2, Marcel Dekker, Inc., New York, N.Y., for example, which is incorporated herein by reference.

In U.S. Pat. No. 6,884,640, issue on Apr. 26, 2005 to Peterson et al., entitled "Method and Apparatus for Determining Layer Thickness and Composition Using Ellipsometric Evaluation," which is incorporated herein by reference, using spectral ellipsometry to determine the composition and thickness of a material layer of a semiconductor device is disclosed.

In a paper by Takeuchi, et al. entitled, "Observation of Bulk $HfO_2$ Defects by Spectroscopic Ellipsometry," in J. Vac. Sci. Technol. A, Jul/Aug 2004, pp. 1337-1341, Vol. 22, No. 4, American Vacuum Society, Research Triangle Park, N.C., which is incorporated herein by reference, detecting defects in films using spectral ellipsometry is disclosed. Spectral ellipsometry was used to detect a defect energy level due to oxygen vacancies within a $HfO_2$ film.

Embodiments of the present invention achieve technical advantages by using spectroscopic ellipsometry and other test methods to detect the quality of films formed on semiconductor devices, wherein the novel test methods are implementable into manufacturing processes. The tests are not destructive, and may be performed on dielectric material layers immediately or soon after they are deposited, rather than later in the manufacturing process flow.

A testing device such as a spectroscopic ellipsometer that uses a monochromatic light source, e.g., that emits radiation of a single wavelength or radiation of a very small range of wavelengths, is used to measure absorption of photon energy over a range of energy levels within the band gap of the material being measured. A spectroscopic ellipsometer does not directly measure the dielectric function of a material. Rather, a spectroscopic ellipsometer measures the ratio of the complex reflectivities of two polarized incident light beams. The imaginary part $\epsilon_2$ of the dielectric function can be calculated from the measured value of the ratio of the complex reflectivities to determine the dielectric function, to be described further herein.

In accordance with embodiments of the present invention, the imaginary part $\epsilon_2$ of the dielectric function $\epsilon(w)$ is calculated and then analyzed to determine if the material has defect states within the band gap. An integral may be taken of the imaginary part $\epsilon_2$ of the dielectric function within the band gap. If the integral exceeds a predetermined threshold level, production may be temporarily halted until the cause of the film defect formation is determined and alleviated, for example.

First, dielectric function of a material will be described. A dielectric function is a fundamental characteristic of a material that describes the response of the material to an applied electromagnetic field. The dielectric function prescribes the optical and electrical property of the material. In general, the dielectric function is a complex function of the applied field energy. The dielectric function $\epsilon(w)$ may be represented by Equation 1:

$$\epsilon(w)=\epsilon_1+(i^*\epsilon_2), \qquad \text{Eq. 1}$$

where $\epsilon_1$ comprises a real part of the dielectric function $\epsilon(w)$, and $\epsilon_2$ comprises an imaginary part of the dielectric function $\epsilon(w)$. The imaginary part $\epsilon_2$ of the dielectric function is correlated to the optical absorption by electrons in the dielectric material, which can be represented by Equation 2:

$$\varepsilon_2 = \frac{1}{4\pi\varepsilon_0}\left[\frac{2\pi e}{mw}\right]\sum_{k_2}|P_{cv}|^2\delta(E_c(k_2^-) - E_v(k_2) - \hbar w) \qquad \text{Eq. 2}$$

where $\epsilon_2$ is the imaginary part of the dielectric function, $\epsilon_0$ is the permittivity of a vacuum, e is the electronic charge, w is the frequency of photon times $2\pi$, $\delta$ is the delta function, $k_2$ is the wave vector, $E_c(k_2)$ is the initial electronic state at $k_2$, $E_v(k_2)$ is the final electronic state at $k_2$, w is the incident photon energy, and $|P_{cv}|$ is the absorption probability of electron from the initial state to the final state. In accordance with embodiments of the present invention, the imaginary part $\epsilon_2$ of the dielectric function is used to characterize a defect state in a dielectric film, to be described further herein.

In general, materials have a conduction band and a valence band. In the conduction band, there are many states for electrons to flow, e.g., when a current is passed through a material. In a valence band, holes flow more freely. Between the conduction band and the valence band is what is referred to in the art as a "band gap," where ideally there is no place for electrons and holes to move, for example. The larger the band gap of a material is, the better an insulator the material is, for example.

FIG. 1 shows an ideal graph 102 of the density of state for an ideal dielectric or insulating material for various energy levels. The graph 102 shows the density of state for $HfO_2$, as an example. The conduction band is represented in the graph 102 at energy levels greater than the conduction band edge $E_c$, and the valence band is represented at energy levels less than the valence band edge $E_v$. The band gap $E_{g1}$ is represented at energy levels between the conduction band edge $E_c$ and the valence band edge $E_v$, for example. In an ideal dielectric material, there are zero density of states for the energy within the band gap $E_{g1}$, as shown.

When photons with energy E are directed onto a dielectric material and the photons are absorbed by the electrons (i.e., non-zero optical absorption occurs), the imaginary part of the dielectric constant $\epsilon_2$ will be a non-zero value at the energy of E. If the energy of E is not absorbed by the dielectric material, the imaginary part $\epsilon_2$ of the dielectric constant is equal to zero. For a perfect dielectric (assuming a temperature of 0 degrees K.), electrons in the valence band can only absorb photon energy that is equal to or greater than the energy difference between its initial state and the next available state. For a perfect dielectric, the next available state with energy larger than the energy of the valence band edge ($E_v$) lies at the conduction band edge ($E_c$), as shown in FIG. 1. Therefore, photon energy (E) less than the band gap energy ($E_c-E_v$, denoted by $E_{g1}$) is not absorbed by the material and as a result, $\epsilon_2=0$ for $E<E_g$.

Figure 2:
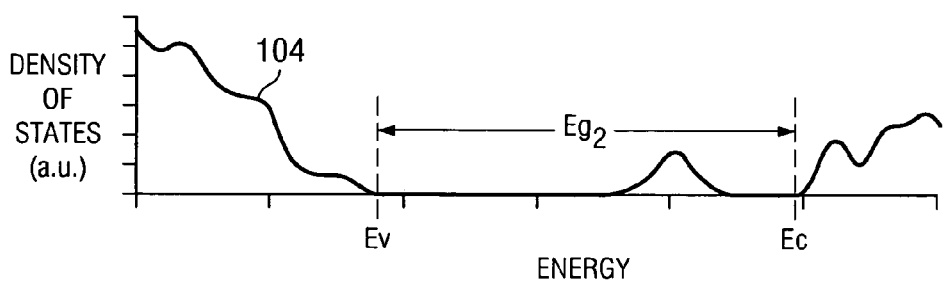
FIG. 2 shows a more realistic density of state graph for an insulating material where defect states such as oxygen vacancies in the dielectric material causes an additional density of states within the band gap and therefore causes a reduced band gap.

However, in reality, there are many kinds of defects that can exist in a material, as shown in FIG. 2, and thus, materials generally do not exhibit the ideal characteristics shown in FIG. 1. FIG. 2 shows a graph 104 of a more realistic density of state graph for an insulating material. The graph 104 shows the density of state for $HfO_{1.875}$, which may be compared to the ideal graph 102 in FIG. 1 of the density of state for $HfO_2$.

Defect states such as oxygen vacancies in the $HfO_2$ material cause an extra density of states within the band gap $E_{g2}$, as shown. Furthermore, the band gap $E_{g2}$ is reduced. For example, the width of $E_{g2}$ is less than the ideal width of the band gap $E_{g1}$ shown in FIG. 1.

The peaks in the graph 104 within the band gap $E_{g2}$ represent defects in the dielectric material, e.g., in the atomic structure of the material, that may be caused by interstitial bonds, impurities, or vacancies, as examples. The defects can contribute to the defect state with energy, which are represented by non-zero values of the graph 104 within the band gap $E_{g2}$. The optical absorption occurs with the photon energy=$E_1-E_v$ which is less than $E_{g2}$, and the imaginary part $\epsilon_2$ of the dielectric function will be a non-zero value at the energy of $E_1-E_v$ (e.g. for less than $E_{g2}$). If the imaginary part of the dielectric constant $\epsilon_2$ is plotted against incident photon energy, for a perfect dielectric, the imaginary part of the dielectric constant $\epsilon_2$ will be a zero value until the incident photon energy is equal to $E_{g2}$. On the other hand, for an imperfect dielectric, there will be a non-zero signal that appears at the energy less than $E_{g2}$. Thus, the imaginary part of the dielectric constant $\epsilon_2$ can be used as a quality signal to characterize the quality of a dielectric film.

Figure 3:
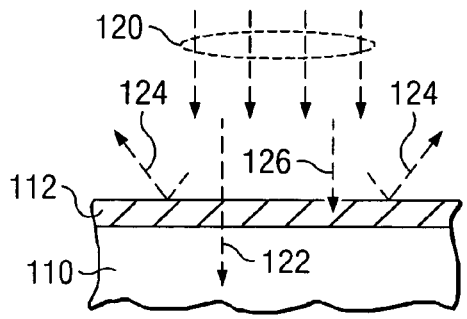
FIG. 3 shows a cross-sectional view of a semiconductor device comprising a workpiece and a material layer such as an insulating layer formed on the workpiece, wherein when light is directed on the material layer, portions of the light are reflected, absorbed, or passed through the material layer.

FIG. 3 shows a cross-sectional view of a semiconductor device comprising a workpiece 110 and a material layer such as an insulating layer 112 formed on the workpiece 110. The workpiece 110 may comprise a semiconductor wafer, for example. When the insulating layer 112 is illuminated with light 120, a portion 122 of the light may pass through the insulating layer 112, a portion 124 may be reflected off of the insulating layer 112, and a portion 126 is typically absorbed, as shown.

Spectroscopic ellipsometry involves illuminating a material layer such as layer 112 with light at a particular energy level at an incident angle, and measuring the absorbed energy to determine qualities of a film. Embodiments of the present invention utilize spectroscopic ellipsometry and other monochromatic light sources to establish systems and methods of analyzing film quality, to be described further herein.

Figure 4:
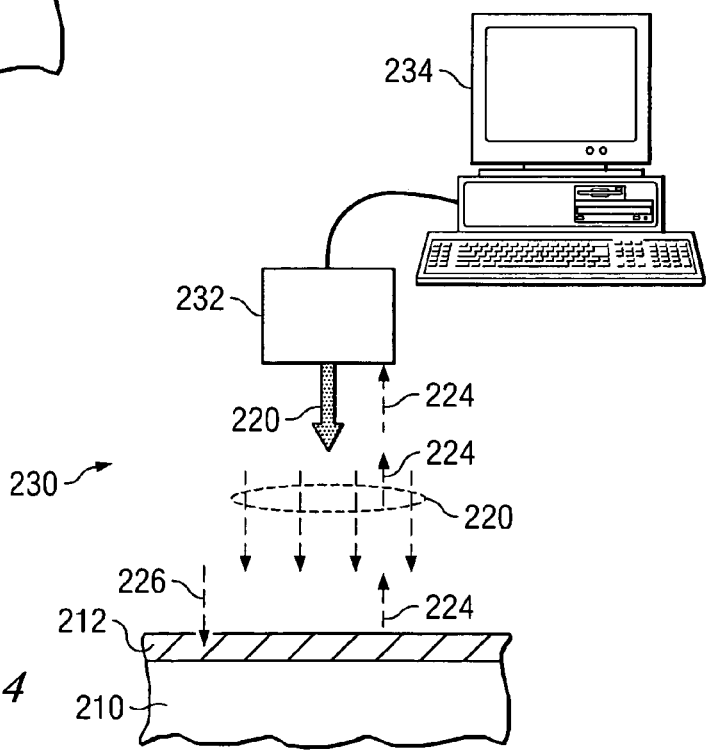
FIG. 4 shows a simplified block diagram of a testing system in accordance with embodiments of the present invention.

Referring next to FIG. 4, there is illustrated a system 230 for testing the quality of material layers of semiconductor devices in accordance with an embodiment of the present invention. The system 230 includes a support means (not shown) for a workpiece 210 having material layer 212 formed thereon. The support means may comprise a chuck, platen, table, or other support, as examples.

A light source and collector 232 is disposed proximate the support means for the workpiece 210, as shown. The light source and collector 232 preferably comprises a monochromatic light source. For example, the light source of the light source and collector 232 may comprise a spectroscopic ellipsometer, which uses a monochromatic light source, or alternatively, the light source may comprise a laser, that uses a monochromatic light with a high energy density. The light source and collector 232 is adapted to transmit light 220 and collect light 224 reflected from an object, namely the material layer 212 formed on the workpiece 210/212, for example. The wavelength of the light source of the light source and collector 232 may be in the ultraviolet range, and alternatively may comprise a photon energy range of about 1 meV to about 100 eV, for example.

The light source and collector 232 may comprise a single device, or may comprise a first device for projecting the light and a separate second device for collecting the light reflected 224, for example. A difference in the light 220 transmitted and the light 224 collected represents the amount of light 226 that is absorbed by the material layer 212, for example. An information processor 234 is coupled to the light source and collector 232, as shown. The information processor 234 may include a computing device adapted to store and process data, for example.

Figure 18:
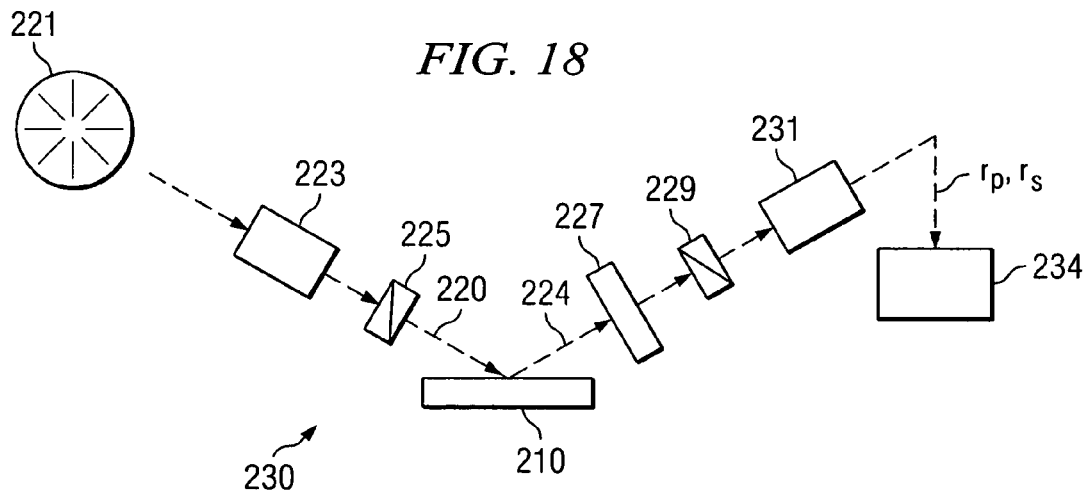
FIG. 18 is a more detailed view of the spectroscopy ellipsometer portion of the testing system shown in FIG. 4.

FIG. 18 shows a more detailed view of the light source and collector 232 shown in FIG. 4. For example, the light source portion of the light source and collector 232 of FIG. 4 may comprise a source 221, a monochromator 223, and a polarizer 225 that are adapted to direct monochromatic polarized light 220 towards the workpiece 210. The light 220 is polarized and thus comprises two light beams comprising an S polarized portion and a P polarized portion, respectively. The light 220 is reflected from the workpiece 210, e.g., as light 224. The light collector portion of the light source and collector 232 of FIG. 4 may comprise a compensator 227, an analyzer 229, and a detector 231, which is adapted to direct the reflected light 224 to the information processor 234. The information processor 234 is adapted to measure or determine the amount of the S and P portion remaining in the reflected light 224, which comprise reflected light $r_S$ and $r_P$.

The reflected light $r_S$ and $r_P$ comprises the information that is collected by the light source and collector 232 or spectroscopic ellipsometer. The reflected light $r_S$ and $r_P$ are used to calculate or model the imaginary part $\epsilon_2$ of the dielectric function. For example, Equation 3 may be used to calculate the dielectric function $\epsilon(w)$:

$$\varepsilon(w) = \sin^2\phi + \sin^2\phi \times \tan^2\phi \times \left[\frac{1-\sigma}{1+\sigma}\right]^2 \qquad \text{Eq. 3}$$

where $\phi$ is the angle of incidence of the light 220 on the material 212, $\sigma$ is the ratio of the complex reflectivities form the two polarized incident light beams S and P, and $\sigma(r_P/r_S$ where $r_P$ is the reflectivity of the P polarized incident light and $r_S$ is the reflectivity of the S polarized incident light.

In accordance with embodiments of the present invention, light at a plurality of energies within a band gap of the material 212 is directed at the material 212, and the measurements are recorded for the reflectivity of the P polarized incident light $r_P$ and the reflectivity of the S polarized incident light $r_S$ at each of the energy levels. The dielectric function $\epsilon(w)$ is then calculated at each of the energy levels. The calculation results of the dielectric function $\epsilon(w)$ comprises a real component and an imaginary component in the format of Equation 4:

$$\epsilon(w)=X+(i*Y), \qquad \text{Eq. 4}$$

where X is the real part and Y is the imaginary part. Thus, Y represents the imaginary component or $\epsilon_2$ of the dielectric function of the material 212 that is measured.

Figure 5:
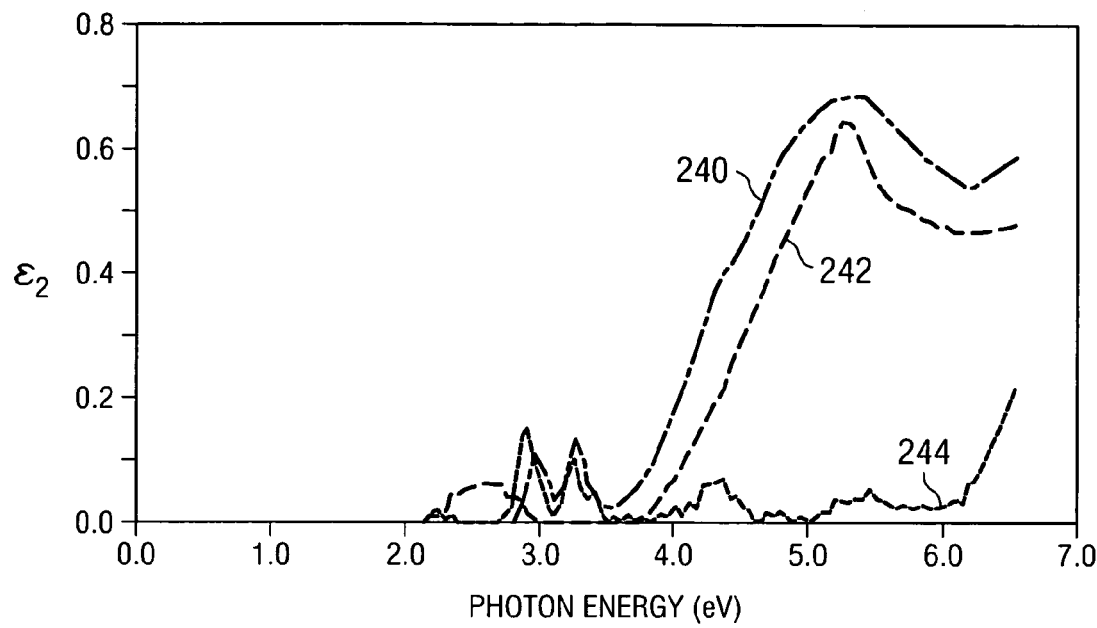
FIG. 5 is a graph illustrating the absorption spectra of three types of insulating materials.

Thus, the imaginary component $\epsilon_2$ of the dielectric function at the range of energy levels tested can be graphed, as shown in FIG. 5, to be described further herein. The process of measuring the reflected light $r_S$ and $r_P$ and calculating the imaginary component or $\epsilon_2$ of the dielectric function of the material 212 described herein together comprise determining the amount of light absorbed by the layer of material 212 at the plurality of energy levels, e.g., within the band gap of the material 212, and thus is representative of the number of defect states and the quantity of defect states of the material 212 within the band gap.

Furthermore, an integral can be calculated of the imaginary component $\epsilon_2$ of the dielectric function over the range of energy levels, and the integral calculated may be used as a metric to quantify or screen the quality of a material layer 212, also to be described further herein. The integral of the imaginary component $\epsilon_2$ of the dielectric function is representative of the number of defect states and the quantity of defect states of the material 212 within the band gap. Threshold values of the integral of the imaginary component $\epsilon_2$ of the dielectric function may be set and used in a manufacturing process flow by periodic testing of wafers under fabrication, for example.

Referring again to FIG. 4, the system 230 may include means for interfacing with an operator of the system 230, such as a display, a panel of controls and indicators, and/or a keyboard, as examples. The system 230 may include an indicator such as an audio or visual indicator to signal a user of the system 230 that an acceptable or unacceptable quality level of the material layer 212 has been detected, for example.

Again, the light source and collector 232 may be adapted to illuminate the material layer 212 disposed on the workpiece 210 with light 220 over a range of energy levels, preferably within a band gap of the material layer 212, for example. The information processor 234 may be adapted to calculate or model the imaginary component $\epsilon_2$ of the dielectric function for each energy level within the range tested, based on the measured reflectivity of the P polarized incident light $r_P$ and the reflectivity of the S polarized incident light $r_S$ at each of the energy levels. The information processor 234 may also be adapted to calculate an integral of the calculated imaginary component $\epsilon_2$ of the dielectric function over the energy levels within the band gap of the material layer 212 tested.

The system 230 may also be adapted to store predetermined values of integral threshold levels. For example, a threshold level of an integral of the imaginary component $\epsilon_2$ of the dielectric function over a predetermined number of a plurality of energy levels within the band gap may be provided and stored for a particular material 212, e.g., in a memory of the information processor 234. The system 230 may also be adapted to compare the calculated integral of the calculated imaginary component $\epsilon_2$ of the dielectric function for the material layer 212 under test with the stored values of integral threshold levels, in some embodiments.

In some embodiments, to implement the system 230, first, a baseline integral of the imaginary component $\epsilon_2$ of the dielectric function over the range of energy levels in the band gap for the material layer 212 is established, e.g., by testing a workpiece 210 having a known acceptable quality level of the material layer 212. For example, the test workpiece 210 may be tested using testing methods other than tests that utilize a spectroscopic ellipsometer, such as electrical tests of devices manufactured with the material layer 212, or other destructive tests on test workpieces 210 manufactured in the same lot or a different lot as the workpiece 210 under test. A library of baseline integrals of the imaginary component $\epsilon_2$ of the dielectric function for a plurality of types of materials 212 may be input by an operator or manufacturer of the system 230 and stored in the memory of the information processor 234, for example.

The system 230 may be implemented in a manufacturing process flow for semiconductors by periodically testing the quality of workpieces 210 having the material layer 212 disposed thereon, by directing light at or illuminating the material layer 212 over a plurality of energy levels within the band gap of the material layer 212, and determining the amount of light absorbed by the layer of material 212 at the plurality of energy levels, e.g., by the light source and collector 232. An integral of the measured amount of light absorbed by the layer of material at the plurality of energy levels may be calculated in some embodiments. The integral of the measured absorbed light is compared to the threshold level of the integral of the absorbed light, e.g., using the information processor 234. The quality of the layer of material 212 is then determined based on the comparison of the integral of the measured amount of absorbed light to the threshold level of the integral of absorbed light. The system 230 may be utilized at periodic intervals comprising quarterly intervals, monthly intervals, weekly intervals, daily intervals, hourly intervals, or less than hourly intervals, after one or more shift changes, or after one or more production lot changes, as examples.

Again, as previously described, determining the amount of light absorbed by the layer of material 212 at the plurality of energy levels preferably comprises measuring reflected light $r_S$ and $r_P$ from the layer of material 212 (e.g., from monochromatic polarized incident light beams S and P directed at the layer of material 212 at the plurality of energy levels in the band gap), and calculating or modeling the imaginary component $\epsilon_2$ of the dielectric function of the material 212 at the plurality of energy levels, in accordance with embodiments of the present invention.

The measurement of the amount of absorbed light may comprise the imaginary component $\epsilon_2$ of the dielectric function, as shown in FIG. 5, which shows the absorption spectra of three types of materials 212. For example, in FIG. 5, a graph of the imaginary component $\epsilon_2$ of the dielectric function is shown at 244 for a material layer 212 comprising $HfO_2$ formed at an oxidation process of 900 degrees C. A graph of the imaginary component $\epsilon_2$ of the dielectric function is shown at 242 for a material layer 212 comprising HfTaTiO, and at 240 for a material layer 212 comprising HfTiO, both of these materials also being formed at an oxidation process of 900 degrees C. Non-zero values of the imaginary component $\epsilon_2$ of the dielectric function indicate defects in the material layer 212 quality, for example.

The band gap of different materials varies from material to material. For example, the conduction band of $HfO_2$ (see 244 in FIG. 5) begins at a higher photo energy level, e.g., about 6.0 eV, than the conduction band of HfTiO (see 240 in FIG. 5), which begins at about 3.5 eV. Thus, there are defect states within the band gap of $HfO_2$ ranging from about 0.0 eV to about 6.0, for example, and defect states exist within the band gap of HfTiO ranging from about 0.0 to about 3.5. In accordance with preferred embodiments of the present invention, the tests and comparisons described herein are preferably performed in incremental steps in the band gap range, e.g., in increments of about 0.1 eV, although alternatively, other increments may be used within the band gap range. In some embodiments, tests are preferably performed close to the band gap edge, e.g., close to the conduction band of the material, to be described further herein.

The results shown in FIG. 5 were measured using a light source and collector 232 (see FIG. 4) comprising a spectroscopic ellipsometer manufactured by J.A. Woollam Co. The quality of the films may be detected by analysis of the graphs 240, 242, and 244 of the imaginary component $\epsilon_2$ of the dielectric function vs. the photon energy (E) in eV. A graph of $\epsilon_2$ vs. E is also referred herein to as a $\epsilon_2$-E spectrum or graph, for example. Defect states within the band gap of high $k_1$ dielectric films may be detected by examining the $\epsilon_2$-E spectrum graphs 240, 242, and 244 shown. If the films are perfect, there should be no absorption (e.g., $\epsilon_2$=0) within the band gap, and the absorption should begin (e.g., to have $\epsilon_2$>0) around the conduction band edge. However, if there are defect states caused by film imperfections within the band gap, there will be absorption ($\epsilon_2$>0) in the band gap.

In particular, it was found that HfTaTiO (see 242 in FIG. 5) has less "in gap" (e.g., in the band gap) defect states compared to HfTiO and $HfO_2$, as can be seen in FIG. 5. HfTiO and $HfO_2$ also have more "near band gap" defect states than HfTaTiO. This observation is consistent with the electrical results discovered using other test methods for correlation with the novel methods of embodiments of the present invention, which showed that HfO$_2$ and HfTiO have higher hysteresis and lower mobility than HfTaTiO. HfTaTiO showed a lower band gap than HfO$_2$, which is also consistent with the EOT-Jg behavior of these films.

The intensity of the imaginary part of the dielectric function $\epsilon_2$ represents the strength of the optical absorption of the material in the band gap, which in effect, indicates the total amount of the defect states in the band gap. Therefore, in some embodiments, the integral of the $\epsilon_2$-E spectrum or graph within at least a portion of the band gap may be integrated. For example, in the $\epsilon_2$-E spectrum shown in FIG. 5, the integral of $\epsilon_2$ for photon energy from E=0 to E=E$_g$, which sums all the non-zero $\epsilon_2$ for the energy below E$_g$ for a material, the $\epsilon_2$-E spectrum indicates the total amount of defect states that exist within the band gap. In other words, the value of the $\epsilon_2$ integral indicatively represents the imperfection of the dielectric film, where a zero value indicates a perfect dielectric.

Furthermore, the integral value calculated may be used as a criterion in production to control the quality of the dielectric material. To be specific, measurements can be taken, and the integral value may be routinely monitored, after the dielectric material deposition process, for every lot, or after production of a number of lots, to ensure the quality of the film. This is advantageous because dielectric material quality may be tested and monitored real-time in a semiconductor production facility.

Figure 6:
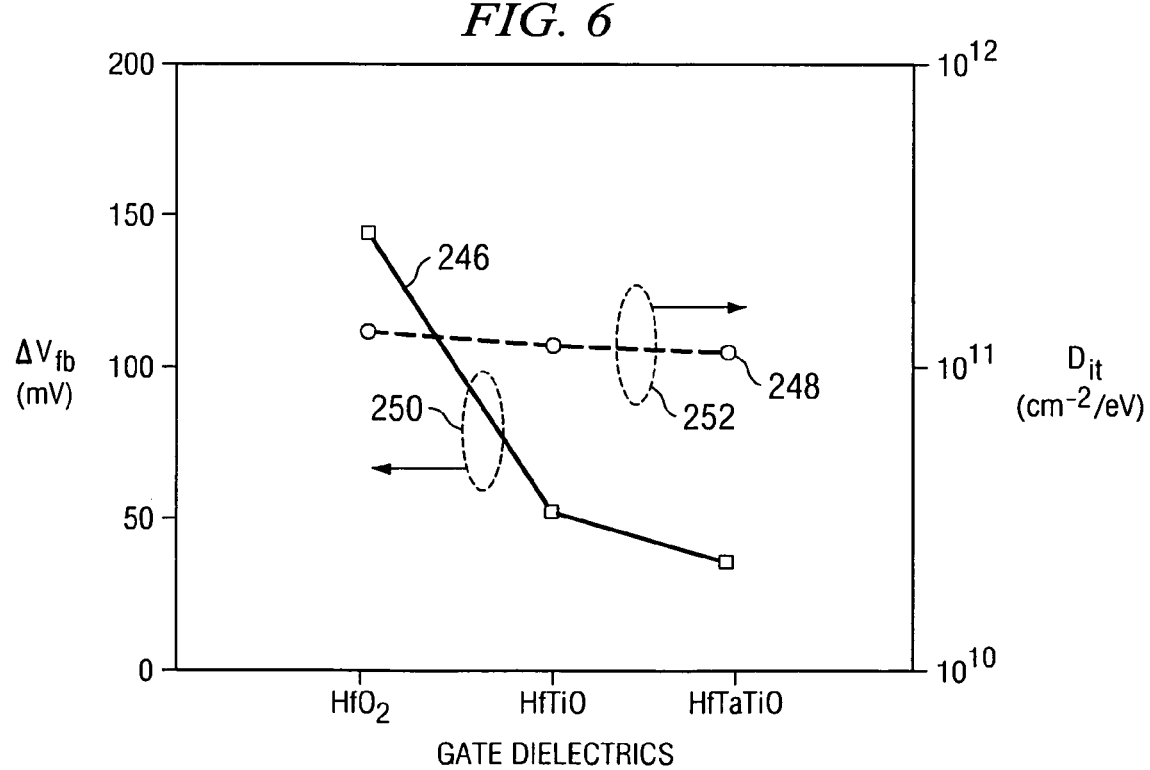
FIG. 6 is a graph showing hysteresis and interface trap density of the three insulating materials shown in FIG. 5.
Figure 7:
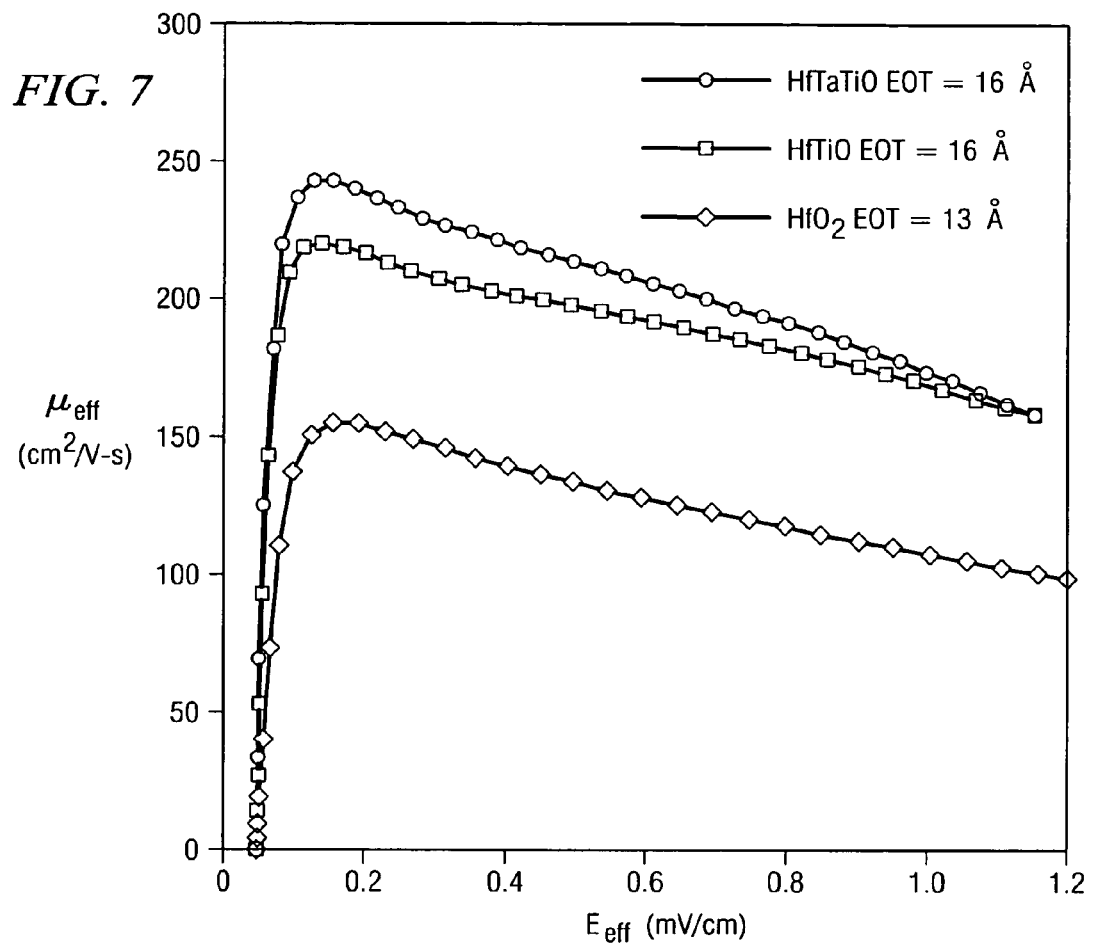
FIG. 7 is a graph showing the electron mobility of the materials shown in FIG. 5.

In FIG. 5, the spectrum difference between these types of materials is shown, and in FIGS. 6 and 7, the electrical behavior of these types of materials is shown. For example, in FIG. 6, the hysteresis ($\Delta V_{fb}$) and interface trap density $D_{it}$ characteristics of the materials shown in FIG. 5 are shown, wherein the $D_{it}$ in cm$^{-2}$/eV is calculated by a Terman method. The flatband voltage $\Delta V_{fb}$ is shown in millivolts (mV). In FIG. 6, line 246 represents the hysteresis ($\Delta V_{fb}$) (which refers to the y-axis on the left-hand side indicated by 250) with respect to the three different gate dielectric materials, and line 248 shows the $D_{it}$ characteristics (which refers to the y-axis on the right-hand side indicated by 252) with respect to the three gate dielectric materials.

From FIG. 6, it can be seen that the hysteresis of HfO$_2$ is the highest of the three films, indicating that HfO$_2$ has more traps in the band gap than the other dielectric materials. This electrical behavior is consistent with the data shown in FIG. 5, where the absorption from HfO$_2$ (line 244 in FIG. 5) exists over a wide energy range below its band gap of about 6.0 eV. The absorption results from the defect states within the band gap and the integral of the $\epsilon_2$ over the energy represents the amount of defect states (or traps) in the HfO$_2$. The hysteresis ($\Delta V_{fb}$) is considered to be related to the bulk traps of the film. The higher $\Delta V_{fb}$ is, the more traps there are in the film, for example. Calculating the integral of measured results of absorbed light in accordance with embodiments of the present invention for these three types of dielectric material yields results that are consistent with the hysteresis ($\Delta V_{fb}$) behavior, which indicate that this technique is valid for film quality detection, for example.

Referring again to FIG. 6, the interface trap density $D_{it}$ characteristics show the quality of interface between the dielectric material 212 and the surface of the workpiece 210, which may comprise silicon, for example. In FIG. 6, interface trap density $D_{it}$ does not have a significant difference among the three types of film which, as a supporting evidence, shows that the hysteresis difference results from the bulk traps and can correspond to the calculated integral values, which are also the bulk properties of the films, for example.

In FIG. 7, the electron mobility $\mu_{eff}$ in cm$^2$/V-s (centimeters squared per voltage per second) versus effective energy E$_{eff}$ in mV/cm of the materials of FIG. 5 are shown for the EOTs of the films indicated, for example.

The novel test results described herein may be used for a quality comparison between different types of films or different lots of the same type of films, for example. The test results may also be used to achieve a quality improvement of the same material. Manufacturing conditions may be varied, and the films may be tested to determine the best quality film and thus the best manufacturing conditions to implement in production, for example. In some embodiments, calculating the integral of the measured absorbed light by the material 212 may not be required, for example, but rather, the measured absorbed light alone is indicative of the quality of the material 212, e.g., indicating the presence of defect states.

In accordance with some preferred embodiments of the present invention, a test utilizing a monochromatic light source is used to detect defects on a material layer of a semiconductor device, and the results are used in the fabrication of semiconductor devices. In one embodiment, for example, a workpiece 210 such as the one shown in FIG. 4 is provided. A material 212 is formed on the workpiece 210, e.g., using chemical vapor deposition (CVD), physical vapor deposition (PVD), or by oxidation and/or nitridation, as examples, although other methods may also be used. The material 212 comprises a dielectric material in one embodiment, although alternatively, the material may also comprise a semiconductive material, for example. The material 212 is formed using a first process condition, in some embodiments. The first process condition may comprise temperature, a type of precursor, pressure, time period, or other variables in the deposition or oxidation/nitridation process used to form the material 212, for example.

The defect state of the material 212 is measured using a test process that utilizes a monochromatic light source such as light source and collector 232 shown in FIG. 4. If the defect state measured is below a predetermined value, then the material 212 is formed on at least one workpiece 210 that may be one of many workpieces 210 in a lot of semiconductor wafers, for example. However, if the detect state measured exceeds the predetermined value, then preferably, the process condition is changed and the test for the defect state of the material 212 is repeated until a process condition is found that results in the achievement of an acceptable defect state of the material 212, for example.

After an acceptable process condition has been found, then the process condition is preferably used to form material layers 212 on a plurality of workpieces 210, e.g., in a manufacturing production facility. The testing of the defect state of the material 212 may be repeated periodically, for example, and if an unacceptable defect state is found, the manufacturing process is preferably discontinued until the process condition or the problem causing the defect state is resolved.

Figure 8:
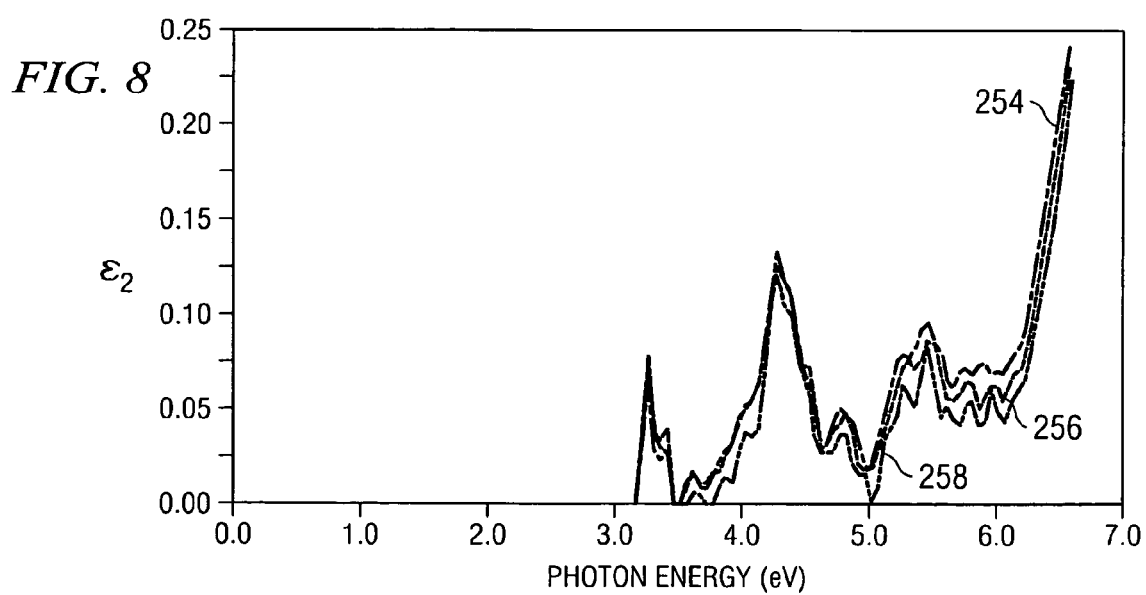
FIG. 8 is a graph showing the absorption spectra of three films formed using different processing conditions.

As an example, in an experiment, the results of which are shown in FIG. 8, three different HfSiO (comprising about 20% SiO$_2$) films were manufactured and tested using three process conditions: a first process condition comprising exposure to O$_3$ with a pulse time of 1.5 seconds, shown at 254; a second process condition comprising exposure to O$_3$ for a pulse time of 2.5 seconds, shown at 256; and a third process condition comprising exposure to O$_3$ for a pulse time of 3.5 seconds, shown at 258. FIG. 8 shows the $\epsilon_2$-E spectrum measured for the three HfSiO films. The graphs 254, 256, 258 indicate that the O$_3$ pulse time is critical in reducing the near-band gap defect states of HfSiO. For example, graph 258 shows lower defect states than graphs 254 and 256, indicating that the optimum process condition for forming HfSiO under these conditions is an exposure to $O_3$ for a pulse time of 3.5 seconds.

Another application of embodiments of the present invention is determining the species concentration in a dielectric material. For some reliability concerns, it is preferable to incorporate species (e.g., N) into a dielectric layer to increase the reliability of the dielectric layer. Even though defect states are created by the species incorporation, the chemical bonding of the species and the atoms in the host material may be stronger and hence may enhance the endurance of the dielectric film during voltage and/or temperature stress. In another aspect, if the defect states that are created by the species incorporation lie well below the conduction band edge of the dielectric, the carriers in the silicon of the workpiece (e.g., such as a workpiece 210 the material 212 is formed on, shown in FIG. 4) could be very difficult to access the defect states and therefore, the existence of the defect states does not negatively impact the operation of the semiconductor device. The concentration of dopant species other than N may be incorporated into the dielectric material may also be determined using the novel test methods and systems described herein. The dopant species incorporated into the material 212 may comprise B, F, As, Sb, P, C, O, Cl, or H, as examples, although the concentration of other dopant species may also be evaluated and quantified using the methods described herein.

For example, N-incorporated HfSiO (or HfSiON) is considered to be a promising Hf-base high dielectric constant material for possible implementation in production. Attempts have been made to tune the N incorporation process (e.g., using a plasma nitridation tool) such that the N concentration in a HfSiON film can reach the optimal electrical performance. Therefore, the detection of the concentration of the incorporated species in the host dielectric material becomes an important application of embodiments of the present invention. Currently, the determination of the concentration level is mostly destructive, and no in-line metrology for the dopant species concentration is available. The test methods and systems described herein that examine the intensity of the imaginary component $\epsilon_2$ of the dielectric function reveal the amount of defect states in the film, and this information can also be used to determine the concentration level of the incorporated species.

Figure 11:
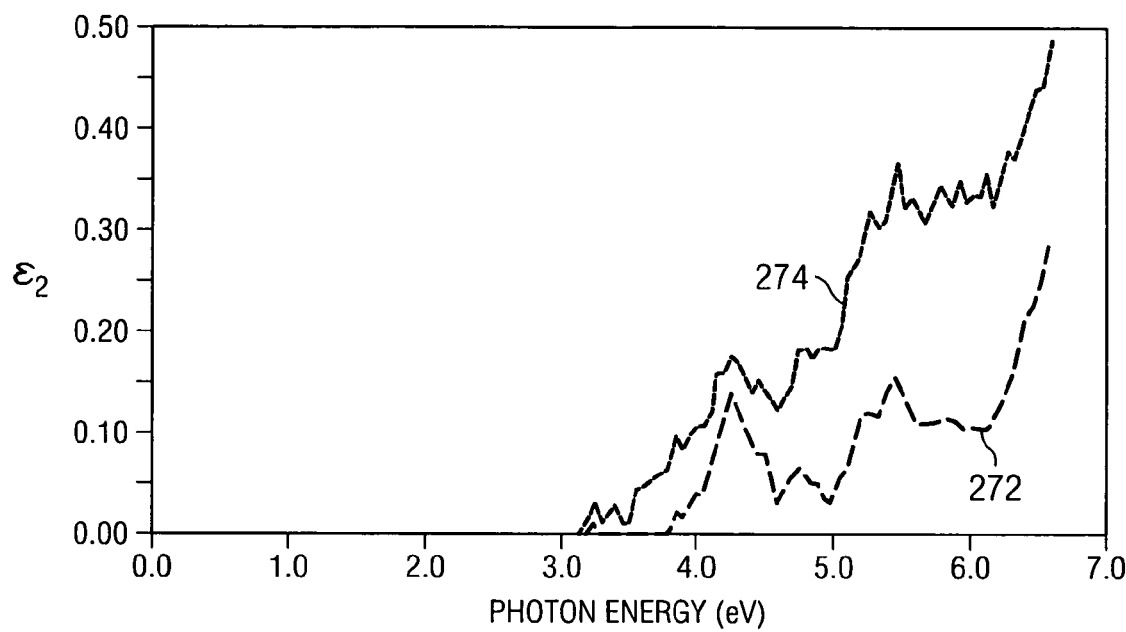
FIG. 11 shows results using the test methods described herein for the films shown in FIGS. 9 and 10.

In addition, the novel test methods described herein are very useful for process development when a species such as N is incorporated into a dielectric material such as HfSiO or $HfO_2$, as illustrated in the graphs shown in FIGS. 9, 10, and 11. The amount of the species (e.g., N) can be detected by the signal obtained in the test results described herein (e.g., the graphs shown were obtained using a spectroscopic ellipsometer). FIGS. 9 and 10 show comparative results by other test methods. In FIG. 9, a SIMS result of the HfSiON film with about 5% of N is shown, and in FIG. 10, a SIMS result of an HfSiON film with about 20% N is shown. FIG. 11 shows results using the novel in-line testing method described herein, e.g., using a spectroscopic ellipsometer. FIG. 11 illustrates the difference between the films shown in FIGS. 9 and 10.

For example, in FIG. 9, 12C+14N is shown at 260, which is the signal from the collected ions (counts/sec) with mass 26. The expression, "12C+14N" at line 260 indicates that an ion with mass 26 was further identified to be one carbon (mass 12) and one nitrogen (mass 14). Similarly, line 262 was identified to be 29Si+14N, and line 264 was identified to be 177HF+14N. In FIG. 10, line 266 was identified to be 12C+ 14N, line 268 was identified to be 29Si+14N, and line 270 was identified to be 177HF+14N. In FIG. 11, $\epsilon_2$-E spectrum test results using a spectroscopic ellipsometer for the film shown in FIG. 9 are shown at 272, and test results for the film shown in FIG. 10 are shown at 274. The test results of the novel test method of the present invention correlate with the test results of the SIMS results shown in FIGS. 9 and 10, as can be seen in the graphs.

Figure 12:
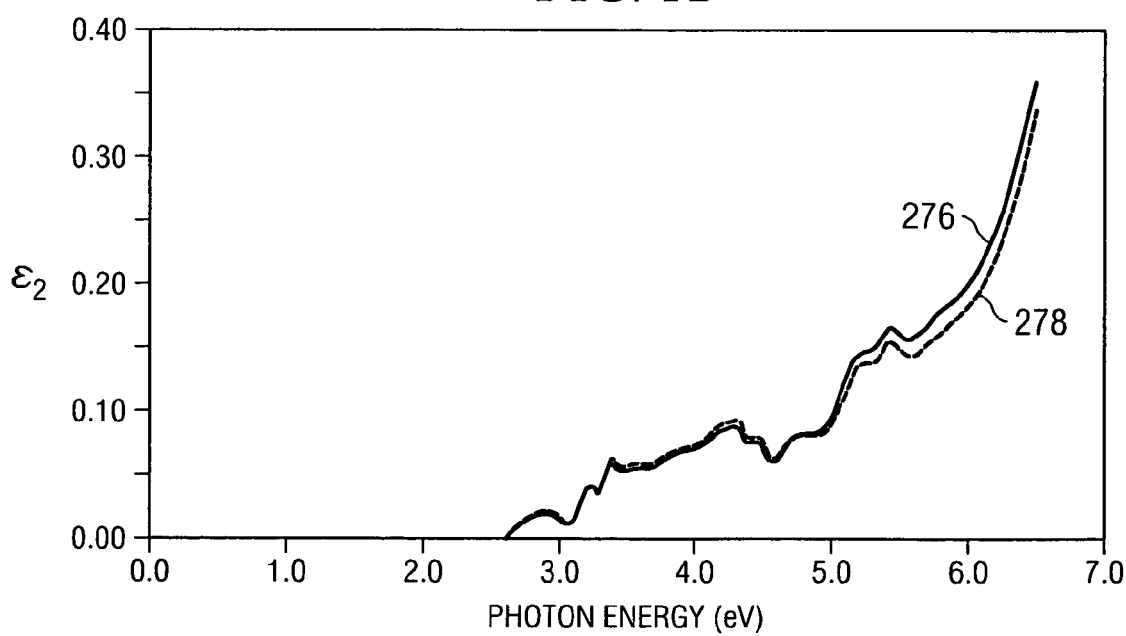
FIG. 12 shows results of the test methods for films formed using two different nitridation processes.

FIG. 12 is a graph showing experimental results of testing two different plasma nitridation conditions used on a layer of $HfO_2$ to form HfON. The graph shows the $\epsilon_2$-E spectrum results using a spectroscopic ellipsometer for the two films processed at the two nitridation conditions, e.g., at 276 and 278. The graphs 276 and 278 indicate that there is no significant N difference between those two processing conditions.

The test methods described herein are useful in comparing test results for one film to test results for another film, and also in comparing test results for a film compared to a baseline threshold. For example, FIG. 13 is a flow chart 280 for establishing a baseline for the test methods described herein, and FIG. 14 is a flow chart 285 for implementing the test method in accordance with an embodiment of the present invention.

Referring to FIG. 13, a baseline threshold for the $\epsilon_2$-E spectrum results may be established by depositing a film (e.g., material 212 shown in FIG. 4) on a workpiece 210 (step 281), and determining $\epsilon_2$-E modeling (step 282) from measured data to dielectric function, using the test methods described herein, e.g., by directing light at the layer of material 212 at a plurality of energy levels, measuring the amount of light absorbed $\epsilon_2$-E by the layer of material 212 at the plurality of energy levels (e.g., by measuring the reflected polarized light $r_S$ and $r_P$, and calculating the imaginary component $\epsilon_2$ of the dielectric function using Eq. 3), and calculating an integral $\Delta\epsilon_2(E)$ of the measured amount of light absorbed by the layer of material 212 at the plurality of energy levels. A plurality of energy levels may first be provided, defining the range and increments for the energy levels of a particular layer of material 212 within a band gap of the layer of material 212, for example.

For example, tests may be performed using other methods on a semiconductor device having the material 212 formed thereon that was manufactured in the same lot. SIMS may be used to determine the defect states of a device for comparison, for example, to ensure that the quality of the film 212 is acceptable as deposited in that particular lot. The test methods described herein then may be used to test a device manufactured in the same lot to determine $\epsilon_2$-E spectrum threshold level, e.g., determining a baseline for the integral of absorbed light at the plurality of energy levels.

Referring again to FIG. 13, the $\epsilon_2$-E modeling and/or $\Delta\epsilon_2$ (E) is integrated into the baseline database (step 283). For example, the integrated result $\Delta\epsilon_2(E)$ comprises a threshold baseline level that may be entered into a database. The results of the integral calculation $\Delta_2(E)$ of the $\epsilon_2$-E model preferably comprises a constant value, such as 5, for example, although the integral calculation may alternatively comprise other constant values, for example.

Several types of materials may be modeled in a similar manner, and the baseline results for each type of material may be stored in the memory of the information processor 234 shown in FIG. 4, for example. Note that before the $\epsilon_2$-E modeling is performed, first, the band gap for each type of material is determined, and the $\epsilon_2$-E modeling is performed over a range of energy levels within the band gap of the particular material.

In some embodiments, the test methods described herein may be used to determine the band gap of a material, for example.

Again, the results of the baseline threshold established may be confirmed using other test methods, such as SIMS, for the initial establishment of the threshold values, for example. Preferably, the baseline threshold establishes a threshold of acceptable defect states in the band gap of the material, for example. For example, the integrated value of the $\epsilon_2$-E model may comprise 3, and the baseline threshold of the integrated value may be set at 5.

The range of energy levels used to establish the baseline may also be stored in the memory of the information processor 234 shown in FIG. 4, along with the integral threshold value for the material 212, for example.

FIG. 14 shows a flow chart 285 of implementing embodiments of the present invention in a manufacturing process for semiconductor devices. A pilot wafer, lot, or shift is selected (step 286), and $\epsilon_2$-E modeling is performed (e.g., $r_S$ and $r_P$ are measured and then $\epsilon_2$ is calculated for each $r_S$ and $r_P$ measured using Eq. 3) on the data measured for the wafer, lot, or shift (step 287) over a predetermined range of energy levels. The results are integrated (e.g., the integral $\Delta\epsilon_2(E)$ of the $\epsilon_2$-E results is calculated) and the $\epsilon_2$-E results are entered into the database (step 288). The integrated results $\Delta\epsilon_2(E)$ are compared with the baseline integral (step 289).

If the calculated integral $\Delta\epsilon_2(E)$ from the tested sample is less than the baseline integral, then production is continued (step 290). However, if the calculated integral $\Delta\epsilon_2(E)$ exceeds the baseline integral, then production is discontinued, and engineering is contacted to intervene in the production process (step 291), preventing the fabrication of additional lots until the problem is addressed. For example, a processing parameter may have inadvertently changed, and the parameter causing the defect states needs to be determined and corrected so that defective devices are not continued to be produced.

In another embodiment, calculating the $\Delta\epsilon_2$ results may be accomplished by making the difference between the $\epsilon_2$ of the "standard" sample and the pilot sample at some preselected energies. The preselected energies may be empirically identified critical defect states that could have a good chance to cause serious failure of the device, for example. In production, it is preferable to monitor the intensity of such critical defects. In this case, the database referred to in step 283 shown in FIG. 13 would need to have acceptance criterion of the intensities of those critical defect states. In FIG. 14, the comparison with the baseline in step 289 is preferably based on the intensities of the selected $\epsilon_2$ signals. The criterion to check the $\epsilon_2$ could be simultaneously imposed, in one embodiment.

In another embodiment, integrating $\epsilon_2$ over E for a predetermined range of energy levels E (the total amount of the critical defects), and then comparing the results with the baseline integral can also be used as another criterion to check the quality. This may be repeated at intervals within the predetermined range of energy levels. The information may be stored as a baseline reference and a tolerance value may be set, e.g., according to experience. For daily inline tests, measurement of the $\epsilon_2$-E for each lot or each shift or at other appropriate periodic test intervals may be performed that it are appropriate for inline quality control purposes, which may depend on tool stability and production load, as examples.

Embodiments of the present invention utilize materials understanding and take advantage of the in-line capability of non-destructive measurement devices such as lasers and spectroscopic ellipsometers to provide a novel in-line metrology for analyzing film quality. Embodiments of the invention may be implemented in software, hardware, or both, for example. The novel test methods and systems described herein may be implemented within spectroscopic ellipsometers, e.g., using additional hardware and/or software, for example, so that the modified spectroscopic ellipsometers may be used in-line in a semiconductor fabrication facility to detect and analyze film quality.

Figure 15:
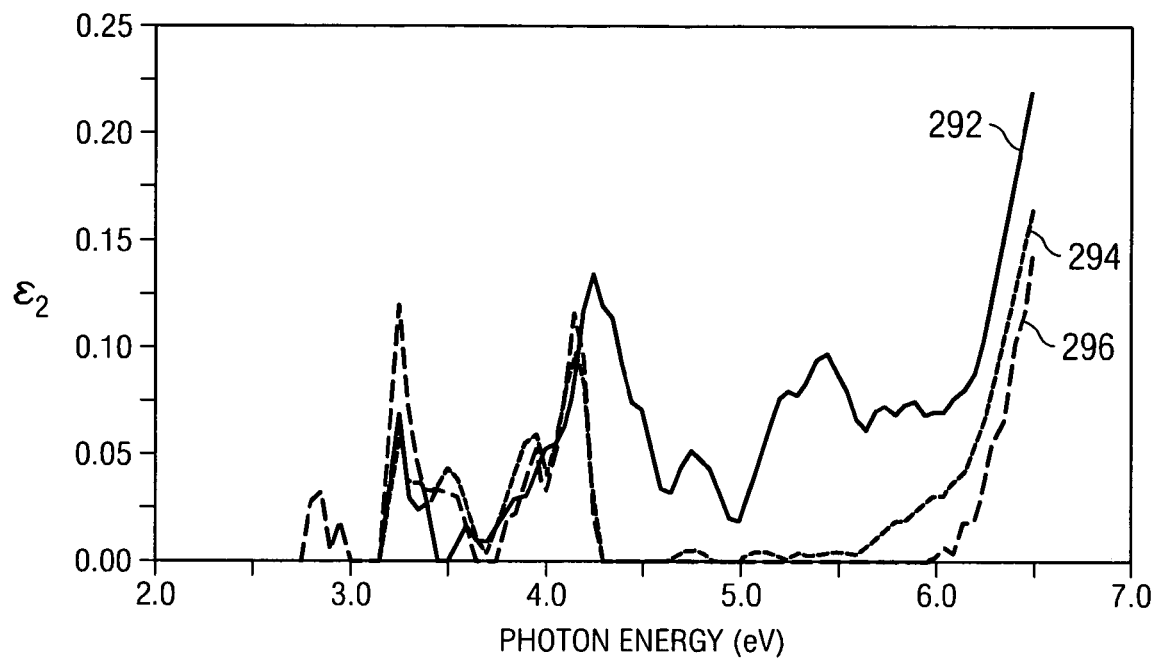
FIG. 15 shows results of the tests performed on the same material at different times.

FIG. 15 shows results of the tests performed on the same material at different times. For example, a baseline $\epsilon_2$-E spectrum 296 is shown at a first time, a $\epsilon_2$-E spectrum 294 is shown at a second time after the first time, and a $\epsilon_2$-E spectrum 292 is shown at a third time after the second time. The $\epsilon_2$-E spectrum in later times 294 and 292 is degraded, and when the baseline $\epsilon_2$-E spectrum 296 is exceeded by an unacceptable tolerance level, then the processing parameters need to be evaluated and corrected, for example.

Figure 16:
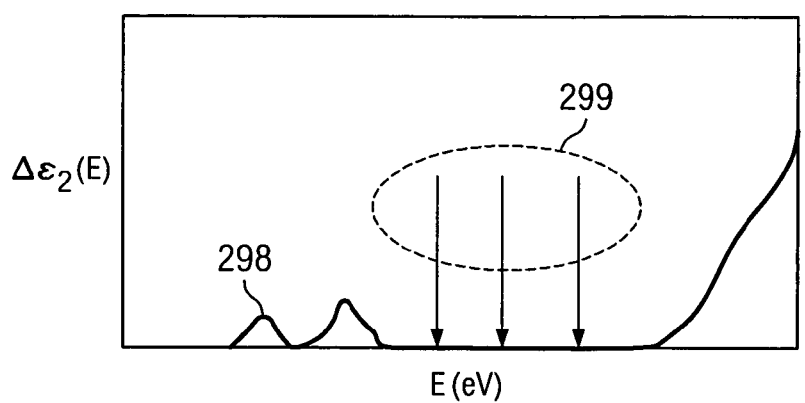
FIG. 16 illustrates several threshold levels that may be established for the test methods.

FIG. 16 illustrates several threshold levels 299 that may be established for the test methods described herein. Defect states are evident in the $\Delta\epsilon_2(E)$ graph at the peaks 298. Criterion may be set for certain energy levels 299 such that the $\Delta\epsilon_2$ of the measured test results of sampled semiconductor wafers may fall within a certain tolerance level without causing concern or disrupting the production of semiconductor devices, for example.

Figure 17:
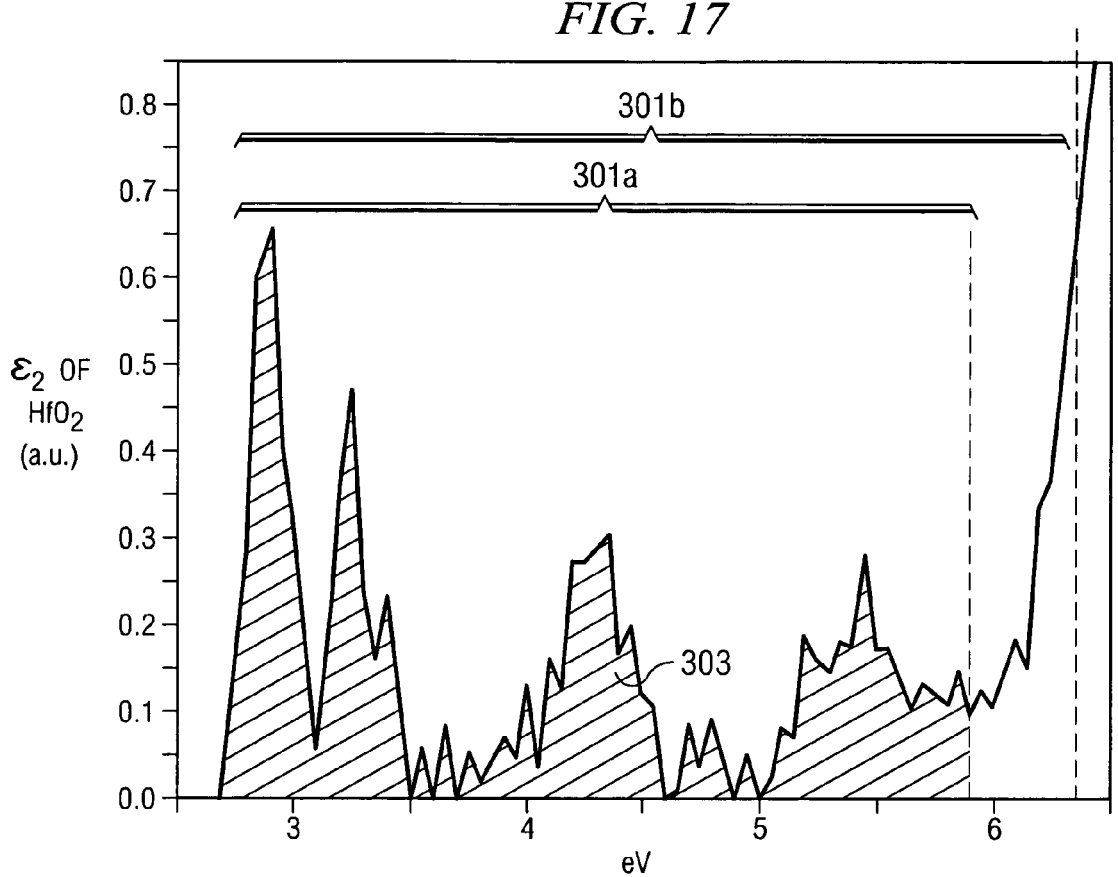
FIG. 17 is a graph illustrating the effect of integrating the measurements of the test results taken in accordance with embodiments of the present invention.

FIG. 17 is a graph illustrating the effect of integrating the measurements of the test results taken in accordance with embodiments of the present invention, e.g., for a $\epsilon_2$-E spectrum model calculated for a layer of $HfO_2$. To illustrate the integral calculation of embodiments of the present invention, test results may be taken of $\epsilon_2$ for a range of energy levels 301*a*, for example, that fall within the band gap of the material 212 under test. The area under the curve 303 is summed to obtain the integral, for example. In accordance with some embodiments of the present invention, preferably the range of energy levels also includes energy levels at the edge of the band gap near the conduction band (e.g., at energy levels greater than about 6.3 eV), as shown at 301*b*, for example. This is an advantage because the "near band-edge defects" are considered to be the most important defects that could affect the electrical performance. The near band-edge defects can be easily charged or discharged by carriers injected from Si (e.g., in the workpiece 210 that the material layer 212 is formed on) or from an electrode (e.g., disposed over the dielectric material 212) during the device operation. When charged (i.e. the carriers are trapped), the charges may affect the Si (e.g., workpiece 210) surface potential and therefore have an impact on the threshold voltage and the drive current, potentially having a deleterious effect on device performance.

Embodiments of the present invention include methods of testing semiconductor devices, methods of testing the quality of material layers formed on semiconductor devices, methods of forming materials of semiconductor devices, and methods of manufacturing semiconductor devices using the novel test methods and systems described herein, as examples. Embodiments of the present invention also include systems for testing semiconductor devices, and fabrication systems for semiconductor devices including the testing systems, for example.

The novel testing systems and methods described herein may be used to find the highest quality films on a real-time basis, e.g., by sampling a wafer from each lot, or evaluating material film quality at other time intervals. High quality dielectric films such as HfSiO, $HfO_2$, and other high dielectric constant materials may be tested for defect states. Optimal conditions for dopant species incorporation may be determined, and the concentration of dopant species may be qualitatively identified quickly using the in-line metrology techniques described herein. The methods may be used to find optimal oxidation conditions, e.g., for PVD-formed dielectric materials. The methods provide the ability to understand semiconductor device performance from a defect state perspective. Furthermore, the methods may assist in understanding the "Fermi-pinning" effect that occurs with some high dielectric constant materials, e.g., which may occur dues to oxygen vacancies and/or dipoles.

Advantages of embodiments of the invention include providing novel test methods for material layers of semiconductor devices and test systems. Embodiments of the invention also include fabrication facilities that utilize the test systems and methods described herein. The quality of material layers may be tested in-line in a manufacturing facility without requiring destructive tests. Because the gate dielectric quality of a transistor may be more carefully monitored and controlled using the test methods and systems described herein, the overall quality of semiconductor devices can be ensured, because a gate dielectric material is one of the most important material layers in semiconductor device fabrication, from a quality perspective. For a research and development facility where new materials, processes, and tools are often evaluated for advanced technologies and new products, the embodiments described herein may also provide a viable way to screen materials, processes, and tools to achieve a high quality of dielectric materials, e.g., to determine appropriate materials, process conditions, and tools.

Although embodiments of the present invention and their advantages have been described in detail, it should be understood that various changes, substitutions and alterations can be made herein without departing from the spirit and scope of the invention as defined by the appended claims. For example, it will be readily understood by those skilled in the art that many of the features, functions, processes, and materials described herein may be varied while remaining within the scope of the present invention. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of testing quality of a material, the method comprising:
    providing a plurality of energy levels, the plurality of energy levels comprising energy levels within a band gap of the material;
    providing a threshold level of an integral of absorbed light at the plurality of energy levels;
    providing a workpiece, a layer of the material being disposed on the workpiece;
    directing light at the layer of material at the plurality of energy levels;
    measuring the amount of light absorbed by the layer of material at the plurality of energy levels;
    calculating an integral of the measured amount of light absorbed by the layer of material at the plurality of energy levels;
    comparing the integral of the measured amount of absorbed light to the threshold level of the integral of absorbed light; and
    determining the quality of the layer of material based on the comparison of the integral of the measured amount of absorbed light to the threshold level of the integral of absorbed light.

2. The method according to claim 1, wherein the material comprises at least one defect state within the band gap, wherein the integral of the measured amount of light absorbed comprises a quantification of the at least one defect state within the band gap.

3. The method according to claim 2, wherein the at least one defect state is disposed at an upper range of energy levels of the band gap, wherein the integral of the measured amount of light absorbed includes the upper range of energy levels of the band gap that includes the at least one defect state.

4. The method according to claim 2, wherein the material comprises a plurality of defect states within the band gap, wherein the integral of the measured amount of light absorbed comprises an indication of the number of defect states within the band gap.

5. The method according to claim 1, wherein providing the threshold level of an integral of absorbed light at the plurality of energy levels comprises providing a threshold level of the integral of the imaginary component $\in_2$ of the dielectric function of the material at the plurality of energy levels; wherein directing light at the layer of material at the plurality of energy levels comprises directing monochromatic polarized incident light beams S and P at the layer of material at the plurality of energy levels; and wherein measuring the amount of light absorbed by the layer of material at the plurality of energy levels comprises measuring reflected light $r_s$ and $r_p$ from the layer of material and calculating the imaginary component $\in_2$ of the dielectric function of the material at the plurality of energy levels.

6. The method according to claim 5, wherein calculating the imaginary component $\in_2$ of the dielectric function of the material at the plurality of energy levels comprises using Eq. 3:

$$\varepsilon(w) = \sin^2\phi + \sin^2\phi \times \tan^2\phi \times \left[\frac{1-\sigma}{1+\sigma}\right]^2 \qquad \text{Eq. 3}$$

where ø is the angle of incidence of the light on the material, σ is the ratio of the complex reflectivities form the two polarized incident light beams S and P, and $\sigma=r_p/r_s$.

7. A system for testing semiconductor devices, comprising:
    a wafer support;
    means for directing light towards a material layer formed on a workpiece disposed on the wafer support;
    means for measuring the amount of light absorbed by the material layer disposed on the workpiece at a plurality of energy levels;
    means for calculating an integral of the amount of light absorbed by the material layer at the plurality of energy levels;
    means for comparing the calculated integral to a predetermined integral threshold level; and
    means for determining the quality of the material layer formed on the workpiece, based on the comparison of the calculated integral to the predetermined integral threshold level.

8. The system according to claim 7, further comprising means for storing the predetermined integral threshold level.

9. The system according to claim 7, wherein the calculated integral indicates whether or not there are defect states in the material layer, further comprising a means for indicating to an operator of the system the presence of an excess amount of defect states of the material layer.

10. A fabrication system for semiconductor devices including the system for testing semiconductor wafers according to claim 7.

* * * * *